United States Patent
Sattler et al.

(10) Patent No.: US 9,943,962 B2
(45) Date of Patent: Apr. 17, 2018

(54) ROBOTIC MEDICAL APPARATUS WITH COLLISION DETECTION AND METHOD FOR COLLISION DETECTION IN A ROBOTIC MEDICAL APPARATUS

(71) Applicants: Stefan Sattler, Forchheim (DE); Stefan Schuster, Forchheim (DE)

(72) Inventors: Stefan Sattler, Forchheim (DE); Stefan Schuster, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 131 days.

(21) Appl. No.: 14/986,722

(22) Filed: Jan. 3, 2016

(65) Prior Publication Data
US 2016/0193731 A1    Jul. 7, 2016

(30) Foreign Application Priority Data

Jan. 2, 2015 (DE) .......................... 10 2015 200 004
Jan. 13, 2015 (DE) .......................... 10 2015 200 355

(51) Int. Cl.
G06F 19/00 (2011.01)
B25J 9/16 (2006.01)
(Continued)

(52) U.S. Cl.
CPC ............. B25J 9/1674 (2013.01); A61B 6/102 (2013.01); A61B 6/4441 (2013.01);
(Continued)

(58) Field of Classification Search
CPC ........... A61B 34/30; A61B 6/54; A61B 6/102; A61B 6/4441; A61B 6/4458;
(Continued)

(56) References Cited

U.S. PATENT DOCUMENTS 5,570,770 A * 11/1996 Baaten .................. A61B 6/102
192/129 A
5,878,112 A * 3/1999 Koertge .................... F16P 3/12
378/209
(Continued)

FOREIGN PATENT DOCUMENTS

CN    101797184 A    8/2010
CN    102028486 A    4/2011
(Continued)

OTHER PUBLICATIONS

Ferman Office Action for German Application No. 10 2015 200 355.8, dated Jul. 29, 2015, with English Translation.
(Continued)

*Primary Examiner* — Rachid Bendidi
(74) *Attorney, Agent, or Firm* — Lempia Summerfield Katz LLC

(57) ABSTRACT

A robotic medical apparatus includes a kinematic chain including a stand unit, an articulation device, a positioning device, and a positionable end effector. The apparatus further includes a controller to control the positioning device. The robotic medical apparatus includes a measurement system to determine a force and/or a torque. The force and/or the torque is essentially acting at one point in the kinematic chain. A measurement signal from the measurement system is transmittable to the controller. The controller is configured to determine the force and/or torque that is acting, and as a function of a current position and/or of a current kinematic state, to determine a nominal force and/or a nominal torque. As a function of the difference between the force that is acting and/or the torque that is acting that has been determined and the nominal force and/or the nominal torque that has been determined, a collision is detected.

12 Claims, 4 Drawing Sheets

(51) Int. Cl.

| | | |
|---|---|---|
| *B25J 19/06* | (2006.01) | |
| *B25J 9/00* | (2006.01) | |
| *B25J 13/08* | (2006.01) | |
| *B25J 15/00* | (2006.01) | |
| *A61B 6/00* | (2006.01) | |
| *A61B 34/30* | (2016.01) | |
| *A61B 6/10* | (2006.01) | |
| *B25J 9/06* | (2006.01) | |

(52) U.S. Cl.
CPC ............ *A61B 6/4458* (2013.01); *A61B 34/30* (2016.02); *B25J 9/0009* (2013.01); *B25J 9/06* (2013.01); *B25J 9/1633* (2013.01); *B25J 9/1676* (2013.01); *B25J 13/085* (2013.01); *B25J 15/0019* (2013.01); *B25J 19/06* (2013.01); *A61B 6/54* (2013.01); *G05B 2219/37624* (2013.01); *G05B 2219/45117* (2013.01); *Y10S 901/09* (2013.01)

(58) Field of Classification Search
CPC ...... B25J 13/085; B25J 15/0019; B25J 19/06; B25J 9/0009; B25J 9/06; B25J 9/1633; B25J 9/1674; B25J 9/1676; G05B 2219/45117; G05B 2219/37624; Y10S 901/09
See application file for complete search history.

(56) References Cited

U.S. PATENT DOCUMENTS

| | | | |
|---|---|---|---|
| 6,550,964 B2 | 4/2003 | Guerit et al. | |
| 7,302,040 B2 * | 11/2007 | Camus | A61B 6/102 378/117 |
| 7,500,784 B2 | 3/2009 | Grebner et al. | |
| 7,564,949 B2 * | 7/2009 | Sattler | A61B 6/102 378/117 |
| 2001/0022831 A1 * | 9/2001 | Meek | A61B 6/102 378/117 |
| 2001/0040940 A1 * | 11/2001 | Guerit | G01N 23/04 378/189 |
| 2004/0042587 A1 * | 3/2004 | Deshpande | A61B 6/105 378/198 |
| 2006/0285644 A1 * | 12/2006 | Camus | A61B 6/102 378/117 |
| 2008/0240363 A1 * | 10/2008 | Grebner | A61B 6/4441 378/198 |
| 2009/0000136 A1 * | 1/2009 | Crampton | B25J 13/088 33/503 |
| 2010/0145515 A1 * | 6/2010 | Nakanishi | B25J 9/1676 700/255 |
| 2010/0191371 A1 | 7/2010 | Hornung et al. | |
| 2011/0072931 A1 * | 3/2011 | Gro | A61B 6/56 74/490.02 |
| 2014/0086393 A1 * | 3/2014 | Graumann | A61B 6/4441 378/198 |

FOREIGN PATENT DOCUMENTS

| | | |
|---|---|---|
| CN | 202143634 U | 2/2012 |
| CN | 3N102688048 A | 9/2012 |
| CN | 103654817 A | 3/2014 |
| DE | 9403972 U1 | 7/1994 |
| DE | 60031277 T2 | 5/2007 |
| DE | 60317419 T2 | 9/2008 |
| DE | 102008005926 A1 | 7/2009 |
| DE | 102008046346 A1 | 3/2010 |
| EP | 2502562 A1 | 9/2012 |
| EP | 2199037 B1 | 1/2013 |

OTHER PUBLICATIONS

Chinese Office Action for Chinese Patent Application No. 201511009691.2 dated May 2, 2017, with English Translation.

* cited by examiner

ROBOTIC MEDICAL APPARATUS WITH COLLISION DETECTION AND METHOD FOR COLLISION DETECTION IN A ROBOTIC MEDICAL APPARATUS

This application claims the benefit of DE 10 2015 200 004.4, filed on Jan. 2, 2015, and DE 10 2015 200 355.8, filed on Jan. 13, 2015, which are hereby incorporated by reference in their entirety.

BACKGROUND

The present embodiments relate to a robotic medical apparatus with collision detection and a corresponding method for collision detection in a robotic medical apparatus.

Medical diagnosis- and intervention systems in angiography, cardiology, neurology and hybrid ORs generally use a C-arm as the mechanical base for the imaging components, such as the X-ray source and X-ray detector. This C-arm may be positioned in a very flexible manner around a patient lying on a patient table for 2D-imaging, for example, assisted by a motorized drive. For 3D-imaging, the C-arm may be moved with semi- or fully automatic movements around the patient in order to acquire a larger number of the individual images that are necessary for the reconstruction. Alongside conventional X-ray stands, in which floor-based or ceiling-based proprietary mechanisms for the positioning of imaging components are used, robotic technology based on industrial robots has been employed for some years for the highly precise positioning and kinematics. Due to the multi-axis kinematics and the associated increase in the degrees of freedom of movement in the system, there is also an increase in system safety requirements. Specifically in a human-robot-collaboration (e.g., in scenarios, in which human and robot not only share the work space but work jointly on something (the patient), there is the risk of impeding each other, with potentially fatal consequences. In order to avoid damage, appropriate safety precautions are to be provided. Alongside the aforementioned C-arm stands, this likewise applies to the patient tables used and also to further statically mounted components of medical systems, such as ceiling mounts, display stands, "booms", other medical arrangements, robotic assistants, or robotic medical instruments. For the aforementioned workspaces, there are no further separating safety devices such that the risk of a collision between the robot and operators is completely ruled out. Consequently, other appropriate safety measures are to be put in place to avoid a collision or a crash or to minimize harmful consequences of a collision, for example, by reducing the speed in the vicinity of a treatment couch. However, since instances of direct contact may occur in a complex environment such as an operating theatre, anywhere and at any time, there remains a residual risk of a collision. An extensive system of sensors is to be provided for this purpose.

Present-day angiography systems generally have various integrated safety mechanisms including, for example, electronic enabling switches known as Dead Man Grips (DMGs), or software-based, collision-detecting measures. An overview is provided hereafter listing safety-support sensors that have also been used hitherto as safety mechanisms.

Through the triggering of electronic switches, collisions on spring-mounted housing components of a C-arm radiation source, or on a C-arm detector with, for example, covering devices in the vicinity of the patient may be detected. Such a solution is known, for example, from U.S. Pat. No. 6,550,964 B2 "Covering device for cover elements which are mobile with relation to the other and radiology machine having such a covering device." Electrical switch strips that may be mounted on the molding of the C-arm may act as resistive switching elements and after an appropriately severe deformation of the switch strip provide a signal that may be used to detect a collision. Suitable switch strips are known, for example, from DE 9403972 U1 "Kantenschutzprofil" [edge protection molding]. A different approach to collision detection is known from U.S. Pat. No. 5,570,770 A1 "Apparatus, in particular an x-ray examination apparatus, with arrangement for collision protection", where in this case, the motor current is monitored by drives in order to detect a collision that has occurred. Acceleration sensors or force sensors based, for example, on strain gauges or magnetic fields are used for collision detection.

Advantageously, these sensors offer a considerable increase in safety. Nevertheless, it is only with difficulty that the sensors may be incorporated extensively, inexpensively and at the same time still in a reliable manner (e.g., on housing components with a complex design). As an example of this, electrical switch strips may be provided. Due to the geometrical shape thereof, the electrical switch strips may only be used individually and only in very limited locations. Even angles of impact greater than 45 degrees may lead to a malfunction. Collisions that occur only a few millimeters next to the strips may not be detected. In order to guarantee full coverage, a largish number of switch strips may be lined up in a row, for example, coated with foam plastic, and the surface may then be finished with an extremely flexible paint. This painted foam cover is very expensive and is not protected from destruction by sharp objects.

A further example is the aforementioned sprung-mounted housing components. These housing components are to function in every spatial position, spatial orientation and at every usual acceleration in movement. This provides that these components are only permitted to have a certain maximum weight, since the restoring force on the housing is too great to trigger in the event of a collision. The switches require an adjustment path. Since the collision with the housing component may likewise occur in this case from various directions, the adjustment path is to be guaranteed in all directions. This may only be achieved by a very complex, mechanically fragile and expensive substructure. In addition, there is the fact that separation lines and consequently edges or grooves are to be provided in order to make this adjustment path available. As a result of this, problems related to hygiene occur in the medical environment with respect to cleaning or to a necessarily expensive seal, for example.

There are also initial developments for flat collision sensors based on piezo films. This technology allows complex geometrical shapes and larger areas or surfaces to be covered. However, the relevant sensor films are to be applied and connected everywhere on the external contours where collisions may occur. This integration into the shell or outer contours is highly complex, and only selected suppliers have mastered the conversion of piezo films.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a robotic medical apparatus with collision detection, which offers a high level of safety compared to known solutions and may be implemented economically, is provided. As another example, an appropriate method for collision detection in a robotic medical apparatus is provided.

A robotic medical apparatus with collision control includes a kinematic chain, is provided. The kinematic chain includes at least one stand unit, at least one articulator (e.g., an articulation device), and an end effector that may be positioned by at least one positioning device. The robotic medical apparatus includes a computation and control device (e.g., a processor) for controlling the at least one positioning device. The robotic medical apparatus includes a measurement system to determine a force and/or a torque. The force and/or the torque essentially acts at a predeterminable point in the kinematic chain. At least one test signal in the measurement system may be transmitted to the computation and control device. The computation and control device is configured to receive the at least one measurement signal from the measurement system and to determine the force and/or the torque that is essentially acting at the one point in the kinematic chain. The computation and control device is configured, as a function of a current position and/or of a current kinematic state, to determine a nominal force and/or a nominal torque at the essentially one point in the kinematic chain. The computation and control device is also configured to detect a collision of the robotic medical apparatus depending on the difference between the force that is acting and/or the torque that is acting that has/have been determined and the nominal force and/or the nominal torque that has/have been determined.

A robotic medical apparatus including a kinematic chain has at least one stand unit, at least one articulation device, and an end effector that may be positioned by at least one positioning device. Such robotic devices, also referred to hereinafter for short as systems that may be used in a medical environment, are known in principle and may, for example, resemble the structure of an industrial robot with a plurality of axes or articulated arms. What is designated as the stand unit is the first link in the kinematic chain, which links the rest of the kinematic chain to the environment (e.g., the floor, a wall, or the ceiling of a treatment room). One or a plurality of articulation devices (e.g., known swivel joints, ball joints, or even linear tracks) may be arranged between the stand unit and the end effector, the final link in the kinematic chain, and further links or articulated arms (e.g., rigid linking supports) may be arranged between the articulation device. Through the at least one positioning device (e.g., an electric motor that is essentially known), the components in the kinematic chain are moveable in a controlled manner (e.g., in directions that are predetermined by the articulation device). Controlled movements lead to a predeterminable positioning of the kinematic chain and the end effectors. A computation and control device (e.g., an electronic circuit or a computer) serves to control the at least one positioning device (e.g., by emitting control signals, such as a targeted change in an electric voltage that is applied to the at least one positioning device), and hence serves to move the kinematic chain. The robotic medical apparatus further includes a measurement system that includes one or a plurality of sensors for determining or supporting the determination of a force and/or a torque. The force and/or the torque is essentially acting at a predeterminable point in the kinematic chain. At least one measurement signal from the measurement system may be transmitted to the computation and control device, for example, by an appropriate data transmitter. For example, the measurement system assists in the determination of a force and/or of a torque at a predeterminable or predetermined point or, in other words, at a specific or central point in the kinematic chain. The measurement system does not generally measure the force and/or the torque at the predetermined point or the central position. In general, there will likewise be forces and torques being applied or acting at other points in the kinematic chain, but these are not measured in this basic concept underlying the present embodiments. At least one measurement signal in the measurement system that is dependent on the force and/or the torque may be transmitted to the computation and control device. The computation and control device is configured to receive the at least one measurement signal from the measurement system and to actually determine the force and/or the torque that is essentially acting at a predeterminable point of the kinematic chain. This provides that the measurement system measures at least one force and/or at least one torque and transmits the measured values to the computation and control device, through which the force and/or the torque that are essentially acting at the predeterminable point in the kinematic chain may be determined. The computation and control device is further configured, as a function of a current position and/or a current kinematic state, to determine a nominal force and/or a nominal torque at the essentially one point in the kinematic chain and, depending on the difference between the force that is acting and/or the torque that is acting and has been determined and the nominal force and/or the nominal torque, to detect a collision of the robotic medical apparatus. Alongside the measurement or determination of the force and/or the torque that is acting at this one point (e.g., the actual state), the computation and control device is able to measure the force and/or the torque in the current position or in the current movement at the point under observation (e.g., the nominal state). The current position in the kinematic chain is known, for example, by incorporating control variables for the at least one positioning device, and the current movement (e.g., speeds, accelerations, etc.) may be determined, for example, from the history of control variables of the at least one positioning device. If the values for the actual and the nominal value differ (e.g., if the difference between the respective values in not equal to zero or is greater than a predeterminable limiting value), an additional force or an additional torque is acting on the robotic medical apparatus, as in the case of a collision. The detection of a collision consequently ensues as a function of the difference between the force that is acting and/or the torque that is acting that has/have been determined and the nominal force and/or the nominal torque that has/have been determined. The additional force or the additional torque does not necessarily impact at the point at which force and/or torque are measured by the measurement system, but may also be applied at another point in the kinematic chain due to the mechanical coupling of the kinematic chain. As a result thereof, extensive collision detection may be achieved at relatively low cost.

In one embodiment, the determination of the force acting at the essentially one point in the kinematic chain and/or of the torque acting at the essentially one point in the kinematic chain and/or of the nominal force acting at the essentially one point in the kinematic chain and/or of the nominal torque acting at the essentially one point in the kinematic chain involves a kinematic model.

The kinematic model may be a mathematical model of the robotic medical apparatus. With the known physical values for the individual components of the robotic medical apparatus (e.g., the geometrical dimensions), the mass distributions and further mechanical properties or material properties, such as, for example, stiffness, a mathematical model of the robotic apparatus may be acquired, for example, using methods of control engineering modeling. The modeling may involve transformation matrices according to Denavit and Hartenberg. Depending on the application, suitable methods range from simple look-up tables to complex differential equations. The input variable in the kinematic model is, for example, the at least one measurement signal in the measurement system, and the output variable is the force and/or the torque acting at the essentially one point in the kinematic chain. Advantageously, the same kinematic model or a further kinematic model may be used to determine the nominal force and/or the nominal torque essentially acting at the one point in the kinematic chain. The input variables are, for example, the current position and/or the current kinematic state of the robotic medical apparatus or regulating variables that are transmitted, by the computation and control device, for example, to the at least one positioning device. The output variable is the nominal force and/or the nominal torque that is essentially acting at the one point in the kinematic chain. The nominal force and/or the nominal torque may also be interpreted as the expected value for force and/or expected value for torque. The calculation of the expected value or these expected values consequently incorporates a model of the mechanical structure of the robotic medical apparatus and/or the material properties of the components of the robotic medical apparatus, and/or the position of the robotic medical apparatus, and/or the movement of the robotic medical apparatus, and/or the acceleration of the robotic medical apparatus.

In a further development, the measurement system includes at least three force sensors and/or at least three torque sensors.

Through this constellation, forces or torques may be measured in three spatial directions or around three spatial axes. From these measurements, the force and/or the torque at the predetermined point may be determined by the computation and control device. Advantageously, the at least three force sensors and/or the at least three torque sensors are arranged to be linearly independent. The selection of the force and/or torque sensors advantageously ensues by the necessary static and dynamic forces in the operation of the system (e.g., the maximum forces plus the allowance for the multiple loads that is required by the standards in order to safely cover the entire dynamic range, including emergency stop scenarios). The measurement system connected to the sensors likewise is to show the entire dynamic range, first in order to avoid exceeding the range of measured values and secondly in order to have a very precise resolution so that the relatively weak signals that are to be detected may be acquired in the event of a slight collision.

In a further embodiment, the at least three force sensors and/or the at least three torque sensors are arranged in a circle and at the same angle from one another.

Through this arrangement, the at least three force sensors and/or the at least three torque sensors may be measured particularly precisely (e.g., if the at least three force sensors and/or the at least three torque sensors are arranged in a plane, and forces and/or torques that are acting on the robotic medical apparatus are acting by a cantilever effect on the force sensors and/or torque sensors of the measurement system).

In one embodiment, the measurement system is arranged between the stand unit and a static surrounding object (e.g., floor, wall, or ceiling).

Since the stand unit is the first link in the robotic medical apparatus, adjacent to which are further links, forces and torques that are acting in any location on the robotic medical apparatus may bring about a change in the measured value from the measurement system. It is consequently possible to cover or monitor the entire system. If the measurement system is arranged in a random location in the system's kinematic chain (e.g., in a different location than between the stand unit and a static surrounding object, such as on a C-arm), it is in generally only possible to partially cover or partially monitor the system. This may also be advantageous if a partial monitoring of the system is required or adequate. In the arrangement of the measurement system, the position thereof is to be known and, for example, is to be trackable via the known axis data, such that the position and location of the sensor coordinate system may be adjusted dynamically. For example, the measurement system or the force sensors may economically consist of three or four standard load cells, on which the system is mounted. This provides that the system is only connected to the mounting plate and hence to the floor, ceiling, etc. via the load cells. This will allow the weight force and the moments around two axes to be calculated.

The measurement system may be arranged in a mounting plate.

In this embodiment, the measurement system is incorporated into a mounting plate. A mounting plate serves to secure the stand unit of the robotic medical apparatus to surroundings (e.g., to the floor of an operating theatre). It may also be said that the kinematic chain is mounted on the sensors of the measurement system. If the measurement system, including force- and torque sensors, is incorporated into the mounting plate, forces and torques may be measured in all directions or around all axes.

In a further embodiment, at least one decoupling device may be arranged between the stand unit and the measurement system.

Significant disturbance variables may occur due to vibrations from external sources. To eliminate these, feet that decouple the system from disturbing vibrations, in a similar manner to loudspeakers, may be inserted, and the desired system forces may be introduced into the force sensors at dedicated locations. The decoupling device serves to reduce the transmission of vibrations from the static surrounding object to the measurement system (e.g., effects a damping of the vibrations).

In an alternative embodiment, the measurement system includes an acceleration sensor to measure accelerations, and accelerations that have been measured are included in the kinematic model.

Since where there is a high system weight, the feet for decoupling that are described above by way of example may not always be ideally designed to be pointed, it may be helpful to fit an additional vibration- or acceleration sensor (e.g., to a surrounding object that is assumed to be static) to the floor or to a mounting plate that is fixedly connected to the floor, which may then absorb the disturbance variables. The effects on the system that are to be expected from the disturbance variables may be calculated by the computation and control device, for example, with the aid of the kinematic model that has been extended accordingly, and consequently be taken into account and compensated for.

Collision detection may be incorporated into the at least one positioning device.

As set out in the aforementioned, recognition or detection of a collision of the robotic medical apparatus with a surrounding object is achieved by comparing the force that is acting and/or the torque that is acting and has been determined and the nominal force and/or the nominal torque that has/have been determined. If for example, the difference is greater than a predeterminable threshold value, a collision is assumed. A simple consideration of the detection of a collision may include, for example, the positioning device being controlled such that the positioning device does not activate any further movement of the robotic medical apparatus and the robotic medical apparatus is "frozen" in motion as it were.

A further development includes the control of the at least one positioning device effecting a reduction in the extent of the difference between the force that is acting and/or the torque that is acting and has/have been determined and the nominal force and/or the nominal torque that has/have been determined.

After the detection of a collision, the at least one positioning device may be controlled such that a reduction in the extent of the difference between the force that is acting and/or the torque that is acting and that has/have been determined and the nominal force and/or the nominal torque that has/have been determined is achieved. This provides that the sensor system in the measurement system and the algorithms that have been worked through with the aid of the computation and control device may also be used recursively alongside the collision monitoring. This provides that it is conceivable to use the forces acting externally such that the system "swerves" into the opposite direction. As an example, if the system moves in the direction of the positive x-axis and suddenly a force acts against the system, the system brakes and may move back again far enough until the force shows "zero" again or has the expected value. This functional principle also operates in downtime. If a force then impacts, for example, because an operator actually handles the system and tries to move the system away, the system may control the position in a force-controlled manner by constantly trying to shift this force towards "zero". The system's degrees of freedom of movement may be very high, which is why these degrees of freedom may be restricted to the pure axis directions. For example, one may allow panning of the system or a linear displacement, but enable a rotation at most by active changing of the movement pattern (e.g., after actuating a key).

In one embodiment, the end effector includes a C-arm with an X-ray emitter and an X-ray image detector.

Robotic medical apparatuses, the final element whereof in the kinematic chain is a C-arm, at each end of which a radiation source, an X-ray emitter, for example, and an X-ray detector or X-ray image detector are arranged, are known from U.S. Pat. No. 7,500,784 B2, for example. Since such an X-ray apparatus has many degrees of freedom and is working in an environment in which moving personnel are also located, the use of one of the collision controls that have been described is particularly highly recommended.

In one or more of the present embodiments, a method for collision detection in a robotic medical apparatus, in which the robotic medical apparatus includes a kinematic chain, is provided. The kinematic chain includes at least one stand unit, at least one articulation device, and an end effector that is positionable using at least one positioning device. The robotic medical apparatus also includes a computation and control device to control the at least one positioning device. The method includes measuring at least one force and/or at least one torque by a measurement system of the robotic medical apparatus, and transmitting at least one measurement signal from the measurement system to the computation and control device. The at least one measurement signal is received from the measurement system by the computation and control device, and a force and/or a torque that is essentially acting at the one predeterminable point in the kinematic chain is determined. Through the computation and control device, a nominal force and/or a nominal torque is determined in the essentially one point in the kinematic chain, and a collision of the robotic medical apparatus is determined as a function of a current position and/or a current kinematic state depending on the difference between the force that is acting and/or the torque that is acting that has/have been determined and the nominal force and/or the nominal torque that has/have been determined.

The process acts may also be carried out in a non-sequential manner. For example, where there is an appropriate time response or timing characteristics, a parallelization may take place in one process act or between two process acts, for example, such that a measured value is acquired. While this is converted and relayed, the next measured value from the sensor is acquired. Where there is adequate computation power, a calculation of the nominal values for future use is already carried out by using a Kalmann filter, for example, such that at the time when the measured value is acquired, a difference is to be formed.

The method may use one of the devices described in the aforementioned.

For example, the determination of the force and/or of the torque acting at the essentially one point in the kinematic chain may ensue with the aid of a kinematic model of the robotic medical apparatus. Process acts that carry out procedures using components of one of the devices according to one or more of the present embodiments that are described in the aforementioned may likewise be provided, such as, for example, the taking into account of accelerations in the kinematic model measured by an acceleration sensor of the measurement system.

In one or more of the present embodiments, the method is carried out automatically, at least in part, and/or repeatedly.

Methods carried out automatically offer the advantage that fewer interventions by an operator are necessary, such interventions often being time-consuming and prone to error. For example, from measured values from the measurement system and the kinematic model, the computation and control device may automatically calculate a force and/or a torque that is acting essentially at a point of the kinematic chain.

The method may be repeated until an abort criterion has been met. An abort criterion may, for example, be interpreted as pushing a button or reaching a predeterminable counter level on a repeat counter. As a result of checking for the abort criterion, the method may be carried out repeatedly. In conjunction with at least partially automatic process acts, a virtually continuous method may be set up.

The exemplary embodiments that are described in further detail hereinafter represent further developments and variants.

DETAILED DESCRIPTION

Figure 1:
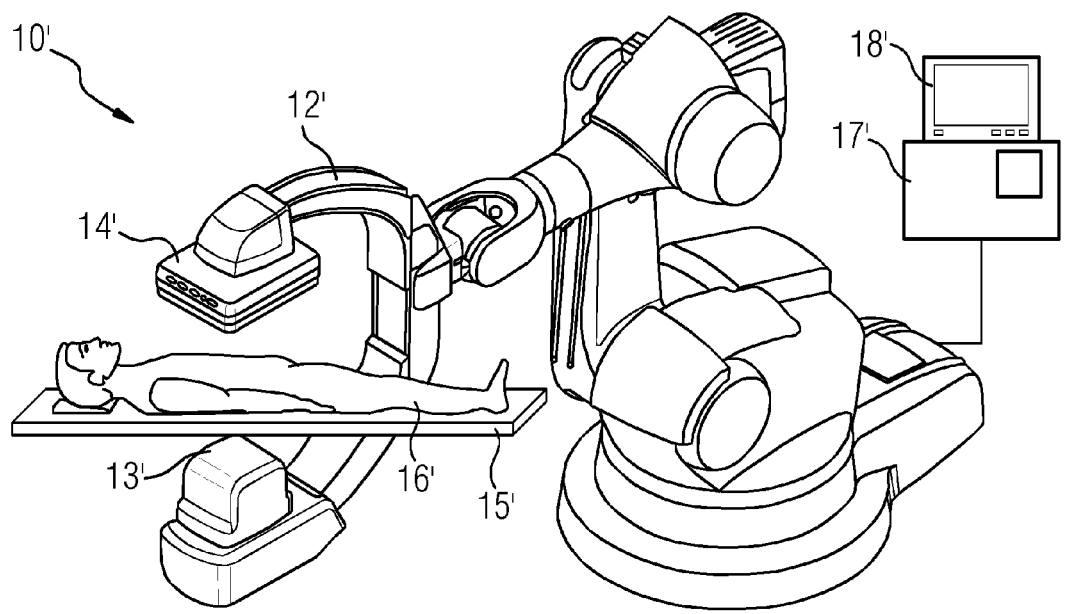
FIG. 1 shows an example of a robotic medical apparatus according to the prior art.

FIG. 1 shows an example of a robotic medical apparatus 10' according to the prior art in the form of an X-ray imaging system including an end effector supported on a stand in the form of a six-axis industrial or articulated robot (e.g., a C-arm 12'), at the ends of which an X-ray source (e.g., an X-ray source 13' with an X-ray tube and collimator) and an X-ray image detector 14' as an image acquisition unit are supported. Using the articulated robot known from U.S. Pat. No. 7,500,784 B2, for example, which includes six rotation axes and hence six degrees of freedom, the C-arm may be spatially moved as desired, for example, by rotating around a center of rotation between the X-ray source 13' and the X-ray image detector 14'. The known articulated robot has a basic frame or stand (e.g., fixedly mounted on a floor). A turntable is attached, rotatably mounted around a first axis of rotation. A robotic swing arm is pivotably mounted on the turntable around a second axis of rotation. A robotic arm is attached such that the robotic arm is rotatable around a third axis of rotation. A robotic hand is rotatably mounted at the end of the robotic arm around a fourth axis of rotation. The robotic hand includes a fixing element for the C-arm. The fixing element is pivotably rotatable around a fifth axis of rotation and around a sixth axis of rotation that runs perpendicular to the fifth axis of rotation. The X-ray image detector 14' may be a rectangular or square, flat semiconductor detector, which may be made from amorphous silicon (a-Si). In one embodiment, integrating and optionally counting CMOS detectors may be used. In the beam path of the X-ray source 13', a patient to be examined is located as an examination subject 16' on a table surface 15' of a patient table. On the X-ray diagnostics apparatus, a system control unit 17' is connected to an image system that receives and processes the image signals from the X-ray image detector 14', operating elements not being shown. The X-ray images may then be observed on a screen 18'.

Figure 2:
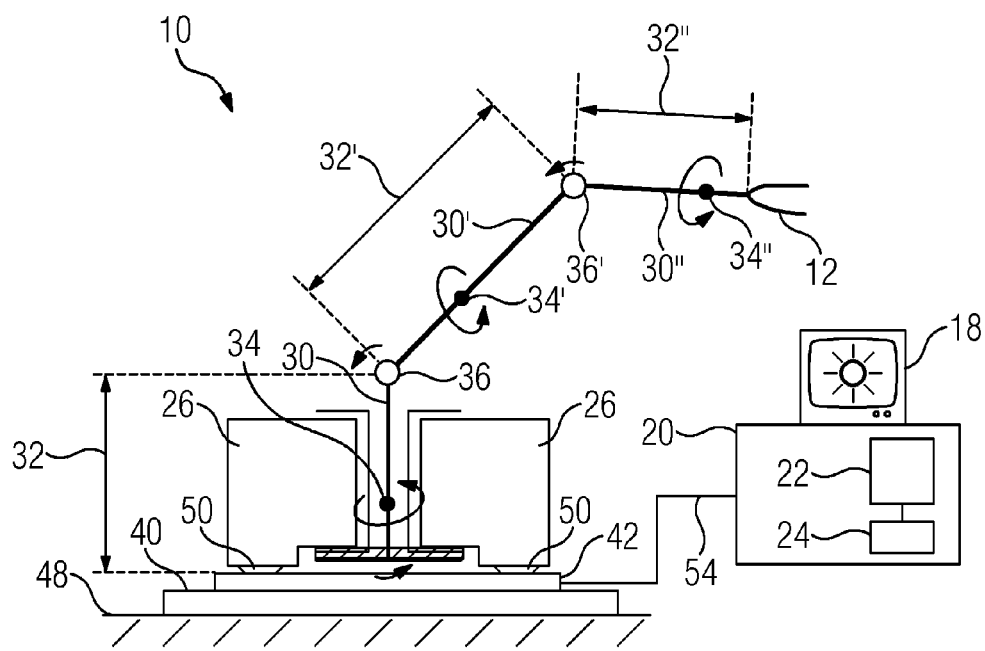
FIG. 2 shows a diagram of one embodiment of a robotic medical apparatus.

FIG. 2 shows by way of example and in diagram form a robotic medical apparatus 10 according to one or more of the present embodiments with collision control. In this exemplary embodiment, the robotic medical apparatus 10 includes a kinematic chain with a stand unit 26, two articulation devices 36 and 36' and an end effector 12, shown symbolically in FIG. 2 as a claw that is positionable using a positioning device that is arranged in the articulation device 36 and 36' and is not shown. The articulation device 36 and 36' is configured as rotary joints and link three rigid articulated arms 30, 30' and 30". The end of the articulated arm 30 that is turned away from the articulation device 36 is connected to the stand unit 26. The stand unit 26, which for mechanical stabilization generally has a considerably greater mass than the rest of the kinematic chain, is connected, via a decoupling device 50 (e.g., three tapered foot-like supports that are arranged in a circle at the same angle) to a measurement system 42 (e.g., shown symbolically as a plate). The measurement system 42 is connected by a mounting plate 40 to a static surrounding object 48 (e.g., the floor). The apparatus 10 further includes a computation and control device 20 (e.g., a computer configured to control the positioning device). The measurement system 42 and, for example, the measurement signals from the measurement system 42 serve to determine a force and/or a torque, with the force and/or the torque essentially acting at a predeterminable point in the kinematic chain. The measurement signals from the measurement system 42 are transmitted to the computation and control device 20 (e.g., by a data transfer device 54 such as a data cable). The computation and control device 20 receives the measurement signals from the measurement system 42 and determines the force that is acting at the one point of the kinematic chain and/or the torque acting at the one point of the kinematic chain. For this purpose, the computation and control device 20 has a kinematic model 24. The kinematic model 24 is in this case a mathematical model of the mechatronics of the robotic medical apparatus 10. With the known physical values for the individual mechatronic components of the robotic medical apparatus 10 (e.g., the geometrical dimensions such as the lengths 32, 32', 32" of the articulated arms 30, 30', 30", the mass, the mass distributions and further mechanical properties or material properties, such as stiffness), a mathematical model of the robotic apparatus may be obtained using methods of control engineering modeling, for example. To illustrate this, in FIG. 2, the centers of gravity of the articulated arms 30, 30', 30" are shown as black dots 34, 34' and 34", and the moments of inertia thereof are drawn in diagrammatically as surrounding arrows. The center of gravity 34 of the first articulated arm 30, for example, may be selected as the one point in the kinematic chain at which the force and/or the torque engages or is active. Measurement signals from the measurement system 42 do not generally measure the forces and/or torques at the center of gravity 34, but with the aid of the forces and/or torques and the kinematic model that have been measured on the decoupling device 50 and transmitted to the computation and control device 20, the forces and/or torques acting at the center of gravity 34 may be determined or calculated. The computation and control device 20 is further configured, as a function of a current position and/or of a current kinematic state, to determine a nominal force and/or a nominal torque at the essentially one point in the kinematic chain (e.g., the selected center of gravity 34) and to establish the difference between the force that is acting and/or the torque that is acting that has/have been determined and the nominal force and/or the nominal torque that has/have been determined. From this difference, the conclusion is drawn that a collision of the robotic medical apparatus 10 with an object that is not part of the apparatus has occurred. If the force and/or the torque that has been determined does not concur with or exceeds the predicted force and/or torque or if the extent of the difference is, for example, greater than a predeterminable threshold value, it may be assumed that an additional force (e.g., a collision) is acting on the apparatus 10. As a result of this, for example, a warning may be issued and displayed on a screen 18. Advantageously, the computation and control 20 includes a computer program 22 that includes the algorithms for collision detection.

Figure 3:
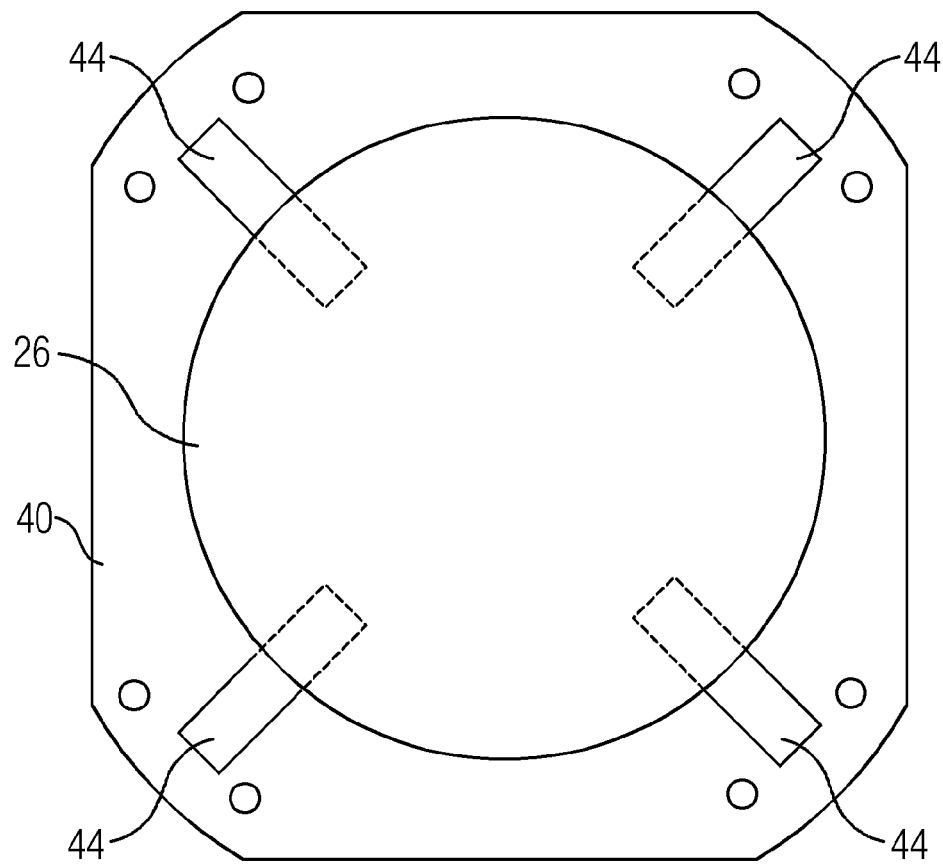
FIG. 3 shows a top view of one embodiment of an arrangement of four force sensors.

FIG. 3 shows, in diagram form, an exemplary embodiment for the arrangement of four force sensors 44 in a top view. In this exemplary embodiment, the four force sensors 44 are economically designed as load cells that are arranged in a circular shape with the same angle of distance between a stand unit 26 and a mounting plate 40. The rest of the kinematic chain, which is not shown, is connected to the stand unit 26. The robotic medical apparatus (e.g., without control and computation device) is therefore only connected to the base of the assembly (e.g., to the mounting plat), and thus to the environment, for example, to the floor, the ceiling or a wall, via the load cells.

Figure 4:
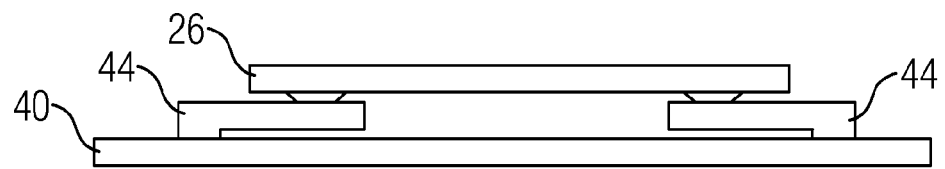
FIG. 4 shows a side view of an exemplary embodiment for the arrangement of four force sensors.

FIG. 4 shows, in diagram form, the exemplary embodiment from FIG. 3, in a side view. The position of the force sensors 44 may be made out between the stand unit 26 and the mounting plate 40. Foot elements that are not shown are arranged between the stand unit 26 and the force sensors 44 in order to achieve a better measurement signal.

Figure 5:
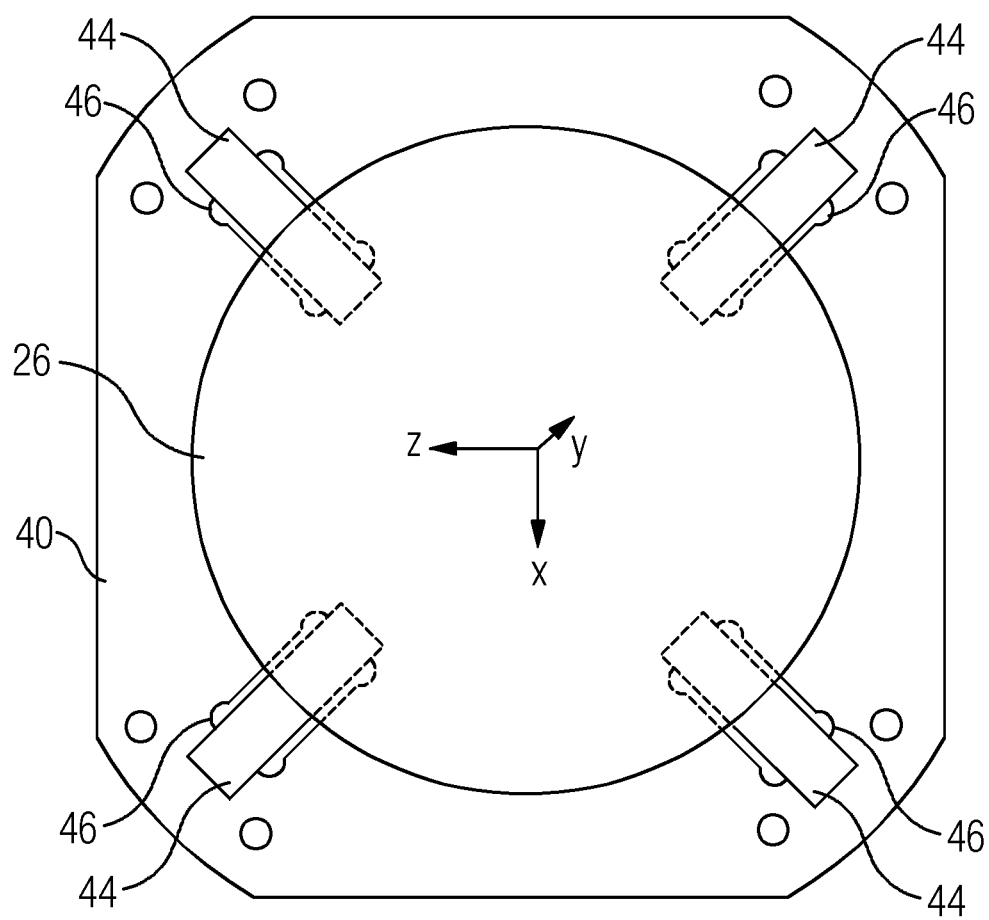
FIG. 5 shows a top view of an exemplary embodiment for the arrangement of four force sensors and four torque sensors in a top view.

FIG. 5 shows, in diagram form, an exemplary embodiment for the arrangement of four force sensors 44 and four torque sensors 46 below a stand unit 26, in a top view. The four force sensors 44 and the four torque sensors 46 are incorporated into a mounting plate 40, making it possible for all six force directions and torque directions to be measured.

Figure 6:
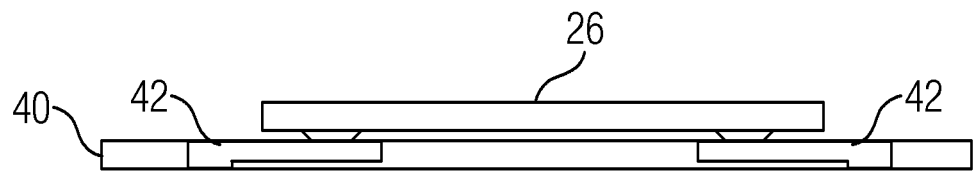
FIG. 6 shows a side view of an exemplary embodiment for the arrangement of four force sensors and four torque sensors.

FIG. 6 shows, in diagram form, the exemplary embodiment from FIG. 5 in a side view. The four force sensors and the four torque sensors form a measurement system 42, which is incorporated into the mounting plate 40 and arranged underneath the stand unit 26.

Figure 7:
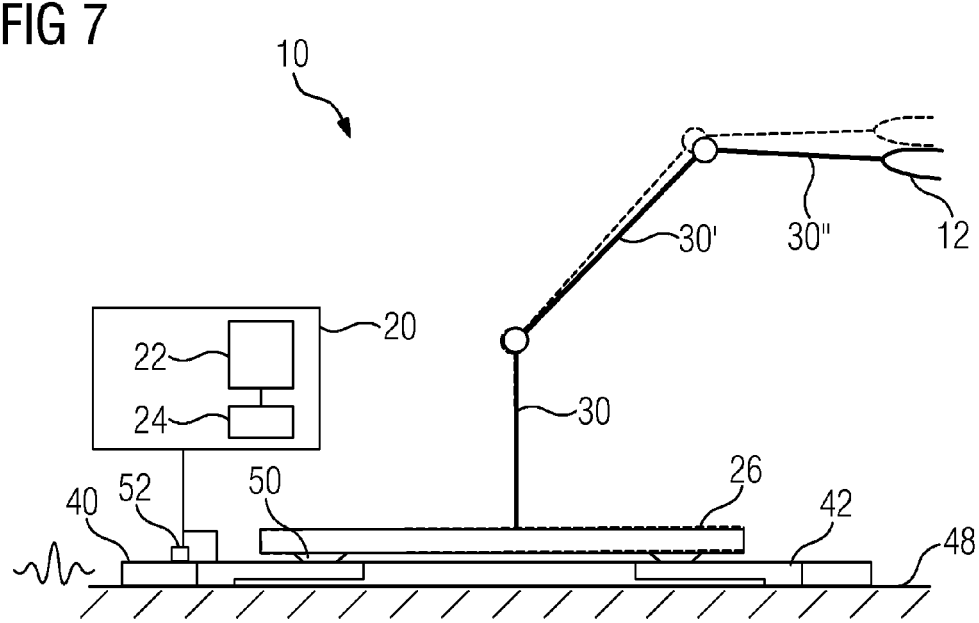
FIG. 7 shows an exemplary embodiment of a part of a robotic medical apparatus including an acceleration sensor.

FIG. 7 shows in diagram form, an exemplary embodiment of a part of a robotic medical apparatus 10 according to one or more of the present embodiments including an acceleration sensor 52. A measurement system 42, which includes force sensors and torque sensors, is again incorporated into a mounting plate 40 and is arranged underneath a stand 26. Three articulated arms 30, 30', 30" and an end effector 12, which are positionable by an articulation device, are connected to the stand unit 26. One disturbance variable that may have an adverse effect on the accuracy of measurement of the measurement system 42 is vibrations due, for example, to a vibrating floor. Due to the law governing levers, slight vibrations in the floor have great effects on the entire system, indicated by the dotted line showing the robotic medical apparatus. In order to eliminate these effects, a decoupling device 50, such as "feet" that decouple the system from disturbing vibrations, in a similar manner to loudspeakers may be inserted, and only the desired system forces may be introduced at locations in the measurement system 42. Since, in the case of a high system weight, for example, the decoupling device 50 may not be sufficiently effective or may not have an ideal design (e.g., not being sufficiently pointed for decoupling), the acceleration or vibration sensor 52 may additionally be attached to a surrounding object that is assumed to be static (e.g., to the mounting plate 40, which is fixedly attached to the floor). With the aid of the acceleration sensor 52, the disturbance variable, indicated in FIG. 7 as a vibration symbol, may be measured. Like the measurement signals from the measurement system 42, the measurement signals from the acceleration sensor 52 are transmitted to a computation and control device 20, which calculates the effects on the system that are anticipated due to the disturbance variables (e.g., with the aid of a kinematic model 24 that has been expanded accordingly). The disturbance variable that has been determined is taken into account or compensated for in the determination of the force and/or torque that is essentially acting at the one point in the kinematic chain. The computation and control device 20 advantageously has a computer program 22 that includes the algorithms to compensate for disturbance variables and to detect collisions.

Figure 8:
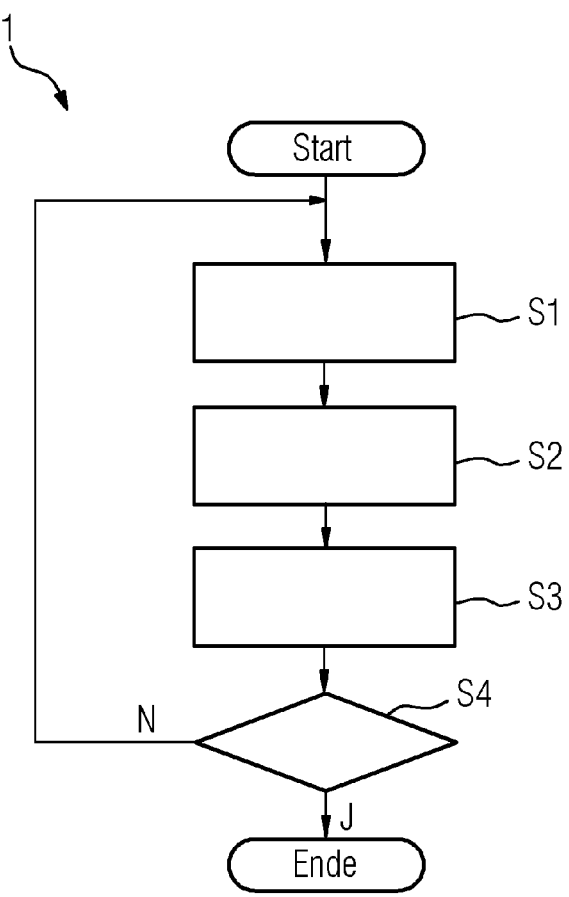
FIG. 8 shows a flow diagram of one embodiment of a method for collision detection in a robotic medical apparatus.

FIG. 8 shows by way of example a flow diagram of a method 1 according to one or more of the present embodiments for collision detection in a robotic medical apparatus. The robotic medical apparatus includes a kinematic chain. The kinematic chain includes at least one stand unit, at least one articulation device, and an end effector that is positionable by at least one positioning device. The robotic medical apparatus includes a computation and control device to control the positioning device. The method 1 includes the process acts S1 to S4. The method begins at "Start", with process act S1 and finishes at "End", according to process act S4. The individual process acts are: S1) Measuring of at least one force and/or at least one torque by a measurement system of the robotic medical apparatus and transmission of at least one measurement signal from the measurement system to the computation and control device; S2) Receiving of the at least one measurement signal from the measurement system by the computation and control device and determination of a force and/or a torque that is acting essentially at a predeterminable point in the kinematic chain; S3) Determination by the computation and control device of a nominal force and/or of a nominal torque at the essentially one point in the kinematic chain, as a function of a current position and/or a current kinematic state, and detecting a collision of the robotic medical apparatus, depending on the difference between the force that is acting and/or the torque that is acting that has/have been determined and the nominal force and/or the nominal torque that has/have been determined; S4) Checking for an abort criterion, and if the abort criterion is not met, if it shows "N", switch to process act S1, otherwise, if "Y", abort the method.

In one embodiment, all or individual process acts are carried out automatically.

To summarize, further variants and advantages of the present embodiments are described. The present embodiments relate, for example, to an under-determined sensor system that is arranged advantageously to the floor or to a mounting point in the kinematic chain, in order to effect full coverage of the movement space for collision detection.

Through the use of force- and/or torque sensors at a central location and appropriate algorithms, a safe, self-monitoring system for collision detection may be constructed. Thus, for example, a sensor arrangement on the mounting plate between the floor and the dynamic system, between the ceiling and the dynamic system, or at any location in the kinematic chain of the system, may serve to monitor the entire system or a partial system. Advantageously, the force sensor system may initially be incorporated at the start of the system's kinematic chain and even combined with the mounting plate. Solutions that only intervene at a later stage in the chain (e.g., in a sensor system), between the C-arm stand base and the C-arm itself, and hence only cover specific parts in the event of a collision, may be equally useful. The geometry of the system and the angle positions that correspond to the axis data are generally known. From these, it is already possible, with a high level of accuracy, to create a model that may be used to calculate forces and torques that may be acting on the force sensor system.

With appropriate algorithms and the kinematic model, the robotic medical apparatus may be monitored safely and with a high degree of precision. The algorithms may include the DH parameters known from the Denavit-Hartenberg transformation matrix (e.g., the angles of the axis and the distances of the axes from one another and the mechanical properties of the parts or components, such as weight, center of gravity, position, mass inertia). From these, an overall center of gravity may be determined at any time, optionally including vibration properties. From this overall center of gravity, forces and torques acting on the sensor coordinate system and hence on the measurement system may be calculated. Both these main components, the sensor system and the algorithms, are flexibly adjustable. This provides that the sensor system, for example, may quickly be adapted to other flange-mounting points, weights, and dynamic influences, such as, for example, higher accelerations. This also applies to the algorithms, which may quickly be adapted, for example, using CAD models that are mostly available, such that further axes or articulated arms may be taken into account. Constant comparison of nominal and actual values allows a safe system in spite of complex algorithms since any deviation, whether it is caused by a collision or by an error in modeling, would lead to a system error state and would therefore be detected. Practical tests have shown that with an apparatus according to one or more of the present embodiments with an overall weight of around 1.5 tonnes, a mathematical collision force resolution of 50 N may already be achieved at a distance of 2 m from the first axis.

In order to minimize external influences, a vibration- or acceleration sensor that measures these influences and calculates the effects thereof through the vibration properties of the individual components may be incorporated.

In principle, this kind of collision detection is also applicable in other fields outside medical technology, such as in the industrial field, for example. One variant may therefore be described as follows. A robotic apparatus with collision control, including a kinematic chain, is provided. The kinematic chain includes at least one stand unit, at least one articulation device, and an end effector that is positionable using at least one positioning device. The robotic apparatus also includes a computation and control device to control the at least one positioning device. The robotic apparatus includes a measurement system to determine a force and/or a torque. The force and/or the torque essentially acts at a predeterminable point in the kinematic chain. At least one measurement signal from the measurement system may be transmitted to the computation and control device. The computation and control device is configured to receive the at least one measurement signal from the measurement system and to determine the force and/or the torque that essentially act at the one point in the kinematic chain. The computation and control device is configured, as a function of a current position and/or a current kinematic state, to determine a nominal force and/or a nominal torque at the essentially one point in the kinematic chain. Depending on the difference derived from the force that is acting and/or the torque that is acting that has/have been determined and the nominal force and/or the nominal torque, a collision of the robotic apparatus may be detected. In addition, one or a plurality of the features described in the aforementioned may be provided by analogy in such a robotic apparatus.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A robotic medical apparatus with collision control, the robotic medical apparatus comprising:
   a kinematic chain comprising:
      a stand unit;
      an articulator; and
      an end effector that is positionable using a positioning device;
   a computation and control device for controlling the positioning device; and
   a measurement system configured to determine a force, a torque, or the force and the torque, wherein the force, the torque, or the force and the torque essentially act at a predeterminable point in the kinematic chain, and wherein at least one measurement signal from the measurement system is transmittable to the computation and control device,
   wherein the computation and control device is configured to receive the at least one measurement signal from the measurement system and to determine a force that is acting, a torque that is acting, or a combination thereof essentially at the one point in the kinematic chain,
   wherein the computation and control device is configured, as a function of a current position, a current kinematic state, or the current position and the current kinematic state to determine a nominal force, a nominal torque, or the nominal force and the nominal torque at the essentially one point in the kinematic chain and, depending on the difference derived from the force that is acting, the torque that is acting, or the force that is acting and the torque that is acting that have been determined and the nominal force, the nominal torque, or the nominal force and the nominal torque to detect a collision of the robotic medical apparatus, and
   wherein a kinematic model is included in the determination of the force that is acting, the torque that is acting, or the force that is acting and the torque that is acting essentially at the one point in the kinematic chain, of the nominal force, the nominal torque, or the nominal force and the nominal torque acting essentially at the one point in the kinematic chain, or a combination thereof.

2. The apparatus of claim 1, wherein the measurement system includes at least three force sensors, at least three torque sensors, or the at least three force sensors and the at least three torque sensors.

3. The apparatus of claim 2, wherein the at least three force sensors, the at least three torque sensors, or the at least three force sensors and the at least three torque sensors are arranged in a circle and at a same angle from one another.

4. The apparatus of claim 1, wherein the measurement system is arranged between the stand unit and a static surrounding object, the static surrounding object being a floor, a wall, or a ceiling.

5. The apparatus of claim 4, wherein the measurement system is arranged in a mounting plate.

6. The apparatus of claim 4, wherein at least one decoupling device is arranged between the stand unit and the measurement system.

7. The apparatus of claim 1, wherein the measurement system includes an acceleration sensor operable to measure accelerations, and
wherein measured accelerations are incorporated into the kinematic model.

8. The apparatus of claim 1, wherein collision detection is incorporated into the control of the positioning device.

9. The apparatus of claim 8, wherein the control of the positioning device brings about a reduction in the extent of the difference between the force that is acting, the torque that is acting, or the force that is acting and the torque that is acting that have been determined and the nominal force, the nominal torque, or the nominal force and the nominal torque that have been determined.

10. The apparatus of claim 1, wherein the end effector includes a C-arm with an X-ray source and an X-ray image detector.

11. A method for collision detection in a robotic medical apparatus, the robotic medical apparatus comprising a kinematic chain, the kinematic chain comprising at least one stand unit, at least one articulation device, and an end effector that is positionable using at least one positioning device, the robotic medical apparatus further comprising a computation and control device to control the at least one positioning device, the method comprising:
  measuring, by a measurement system of the robotic medical apparatus, at least one force, at least one torque, or the at least one force and the at least one torque and transmitting at least one measurement signal from the measurement system to the computation and control device;
  receiving, by the computation and control device, the at least one measurement signal from the measurement system and determining a force, a torque, or the force and the torque that are essentially acting at a predeterminable point in the kinematic chain; and
  determining, through the computation and control device, a nominal force, a nominal torque, or the nominal force and the nominal torque at the essentially one point in the kinematic chain, and detecting a collision of the robotic medical apparatus as a function of a current position, a current kinematic state, or the current position and the current kinematic state depending on a difference derived from the force that is acting, the torque that is acting, or the force that is acting and the torque that is acting, and have been determined and the nominal force, the nominal torque, or the nominal force and the nominal torque that have been determined,
  wherein a kinematic model is included in the determining of the force that is acting, the torque that is acting, or the force that is acting and the torque that is acting essentially at the one point in the kinematic chain, of the nominal force, the nominal torque, or the nominal force and the nominal torque acting essentially at the one point in the kinematic chain, or a combination thereof.

12. The method of claim 11, wherein the method is at least partially carried out automatically, repeatedly, or automatically and repeatedly.

* * * * *